US012508147B2

(12) United States Patent
Chen

(10) Patent No.: US 12,508,147 B2
(45) Date of Patent: Dec. 30, 2025

(54) REHABILITATION BOOT

(71) Applicant: Tung Cheng Chen, Taichung (TW)

(72) Inventor: Tung Cheng Chen, Taichung (TW)

( * ) Notice: Subject to any disclaimer, the term of this patent is extended or adjusted under 35 U.S.C. 154(b) by 162 days.

(21) Appl. No.: 18/625,493

(22) Filed: Apr. 3, 2024

(65) Prior Publication Data

US 2025/0312183 A1 Oct. 9, 2025

(51) Int. Cl.
*A61F 5/058* (2006.01)

(52) U.S. Cl.
CPC .................................. *A61F 5/0585* (2013.01)

(58) Field of Classification Search
CPC .... A61F 5/0585; A61F 5/05841; A61F 5/058; A61F 5/05; A61F 5/04; A61F 5/01; A61F 5/00; A61F 5/0102; A61F 5/0127
See application file for complete search history.

(56) References Cited

U.S. PATENT DOCUMENTS

2020/0345530 A1* 11/2020 Natsis .................. A61F 5/0127

FOREIGN PATENT DOCUMENTS

CN 101965168 B * 7/2012 ........... A61F 5/0585
CN 109394403 A * 3/2019 ........... A61F 5/0127

* cited by examiner

*Primary Examiner* — Tarla R Patel
(74) *Attorney, Agent, or Firm* — patenttm.us

(57) ABSTRACT

A rehabilitation boot has a main body, a front plate, and two restricting bands. The main body has a base and a tubular sleeve. The base has a front end and a rear end opposite to each other. The tubular sleeve is integrally formed at the base and has an opening and two cuts. The opening is disposed at a front side of the tubular sleeve. The two cuts longitudinally extend from a top of the tubular sleeve to the base to divide the tubular sleeve into a rear plate and two lateral plates respectively disposed at two opposite sides of the rear plate. The front plate is connected to the main body via multiple elastic bands. One of the restricting bands connects with the rear plate and one of the lateral plates, and the other restricting band connects with the rear plate and the other lateral plate.

13 Claims, 6 Drawing Sheets

REHABILITATION BOOT

BACKGROUND OF THE INVENTION

1. Field of the Invention

The present invention relates to an orthopedic device, and more particularly to a rehabilitation boot that can be adjusted according to recovery conditions.

2. Description of Related Art

Traditionally, plaster casts are used to hold broken limbs, such as broken arms and broken calves, in position. However, once a plaster cast is fixed to a broken limb, it cannot be adjusted again corresponding to recovery conditions of the broken limb.

In order to solve the above deficiency of the plaster cast, rehabilitation boots are invented for patients having broken calves. A conventional rehabilitation boot has a tubular sleeve, a front plate, and elastic ribbons. The tubular sleeve is configured to wrap a broken calf of a patient and has an opening disposed at a front side of the tubular sleeve. The front plate is connected to the tubular sleeve via the elastic ribbons and covers the opening of the tubular sleeve.

Though the tubular sleeve surrounding the broken calf can hold the broken calf in position as well, the tubular sleeve is hard to be expanded when the broken calf swells. Therefore, the swelling and broken calf is pressed by the tubular sleeve and causes an uncomfortable feeling of the patient.

To overcome the shortcomings of the conventional rehabilitation boot, the present invention provides a rehabilitation boot to mitigate or obviate the aforementioned problems.

SUMMARY OF THE INVENTION

The main objective of the present invention is to provide a rehabilitation boot that provides patients having broken limbs with comfortable experiences.

The rehabilitation boot has a main body, a front plate, and two restricting bands. The main body has a base and a tubular sleeve. The base has a front end and a rear end opposite to each other. The tubular sleeve is integrally formed at the base and has an opening and two cuts. The opening is disposed at a front side of the tubular sleeve. The two cuts longitudinally extend from a top of the tubular sleeve to the base to divide the tubular sleeve into a rear plate and two lateral plates respectively disposed at two opposite sides of the rear plate. The front plate is connected to the main body via multiple elastic bands. One of the restricting bands connects with the rear plate and one of the lateral plates, and the other restricting band connects with the rear plate and the other lateral plate.

Other objects, advantages, and novel features of the invention will become more apparent from the following detailed description when taken in conjunction with the accompanying drawings.

DETAILED DESCRIPTION OF PREFERRED EMBODIMENTS

Figure 1:
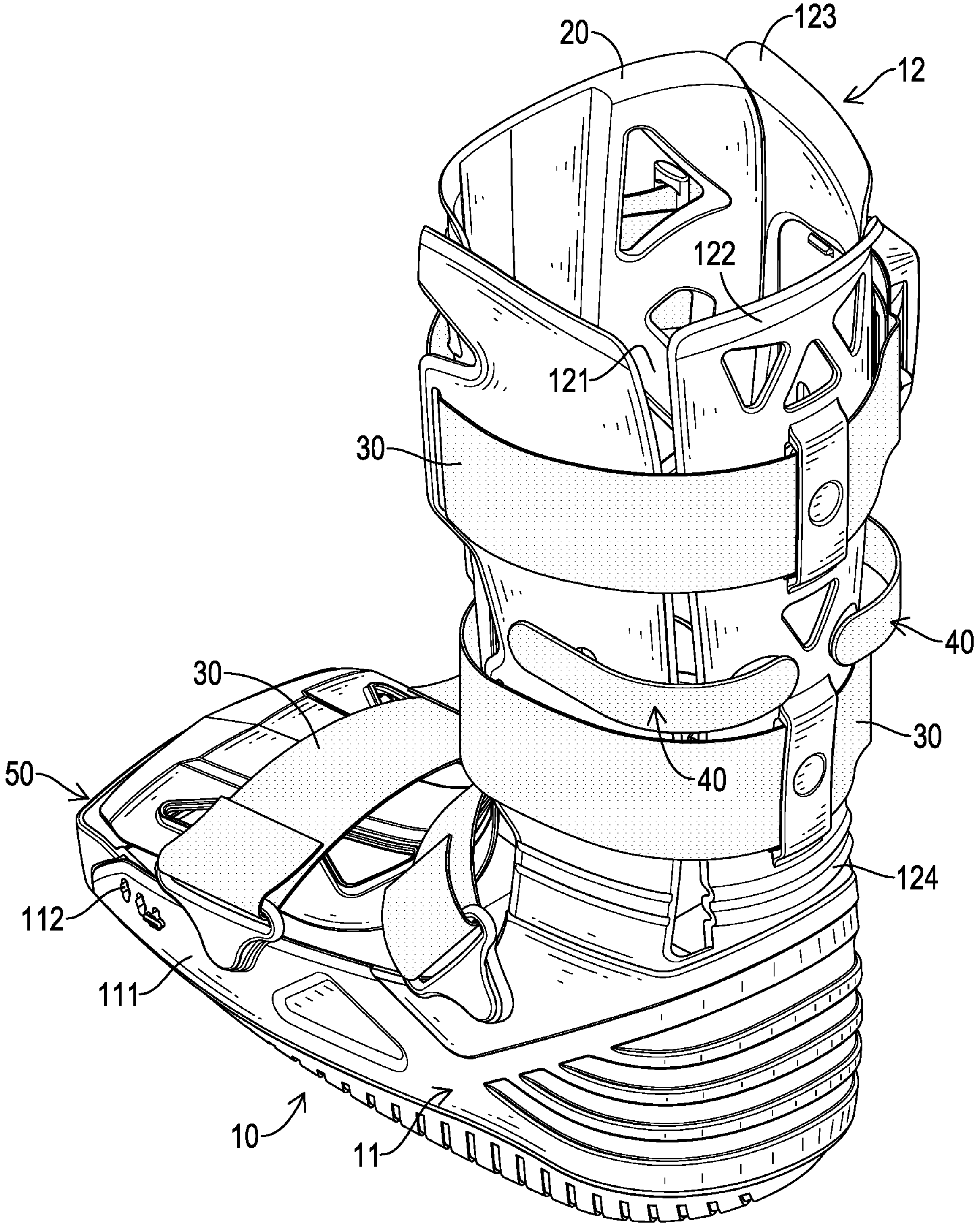
FIG. 1 is a perspective view of a rehabilitation boot in accordance with the present invention.
Figure 2:
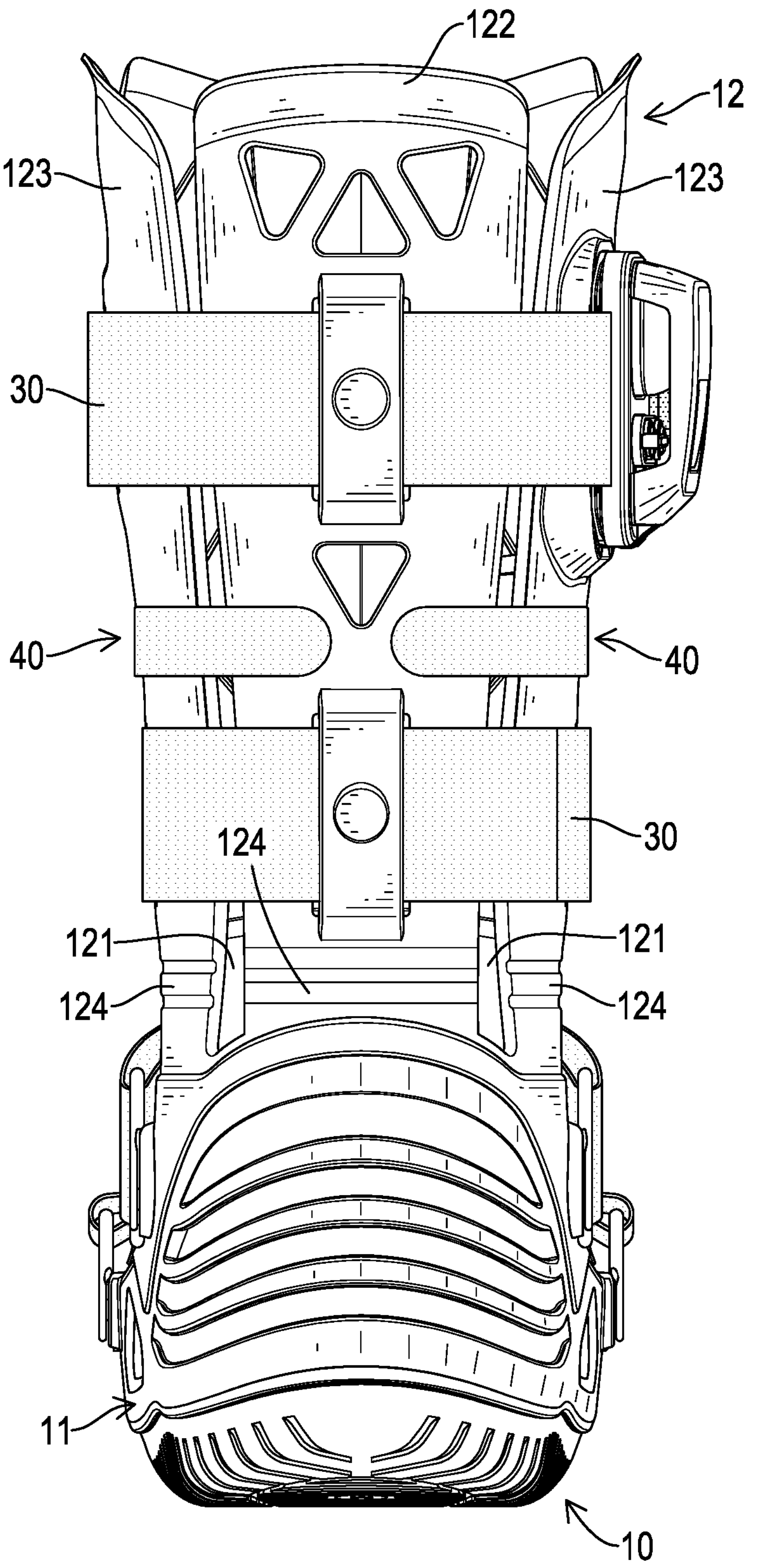
FIG. 2 is a rear side view of the rehabilitation boot in FIG. 1.
Figure 3:
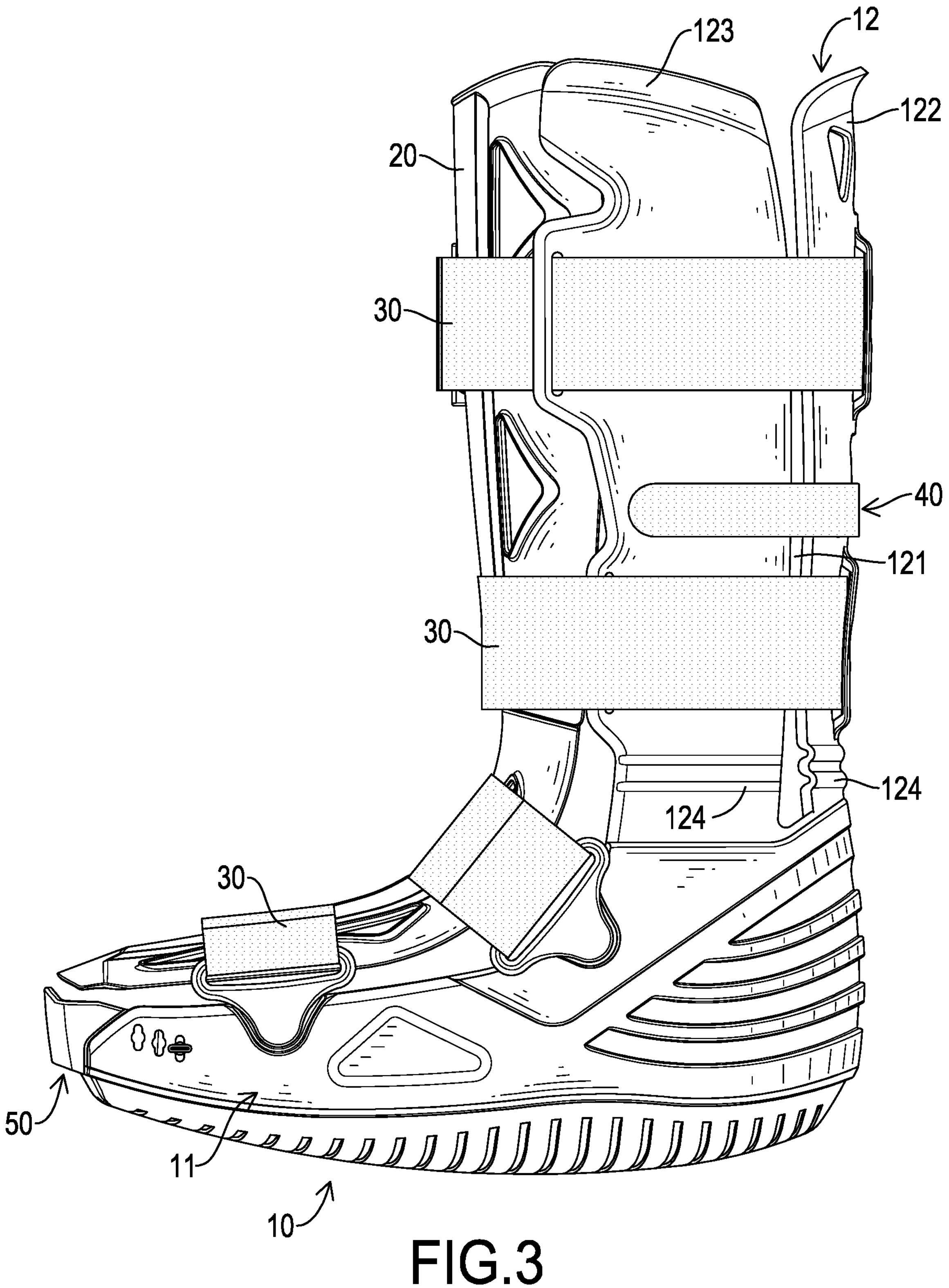
FIG. 3 is a lateral side view of the rehabilitation boot in FIG. 1.
Figure 4:
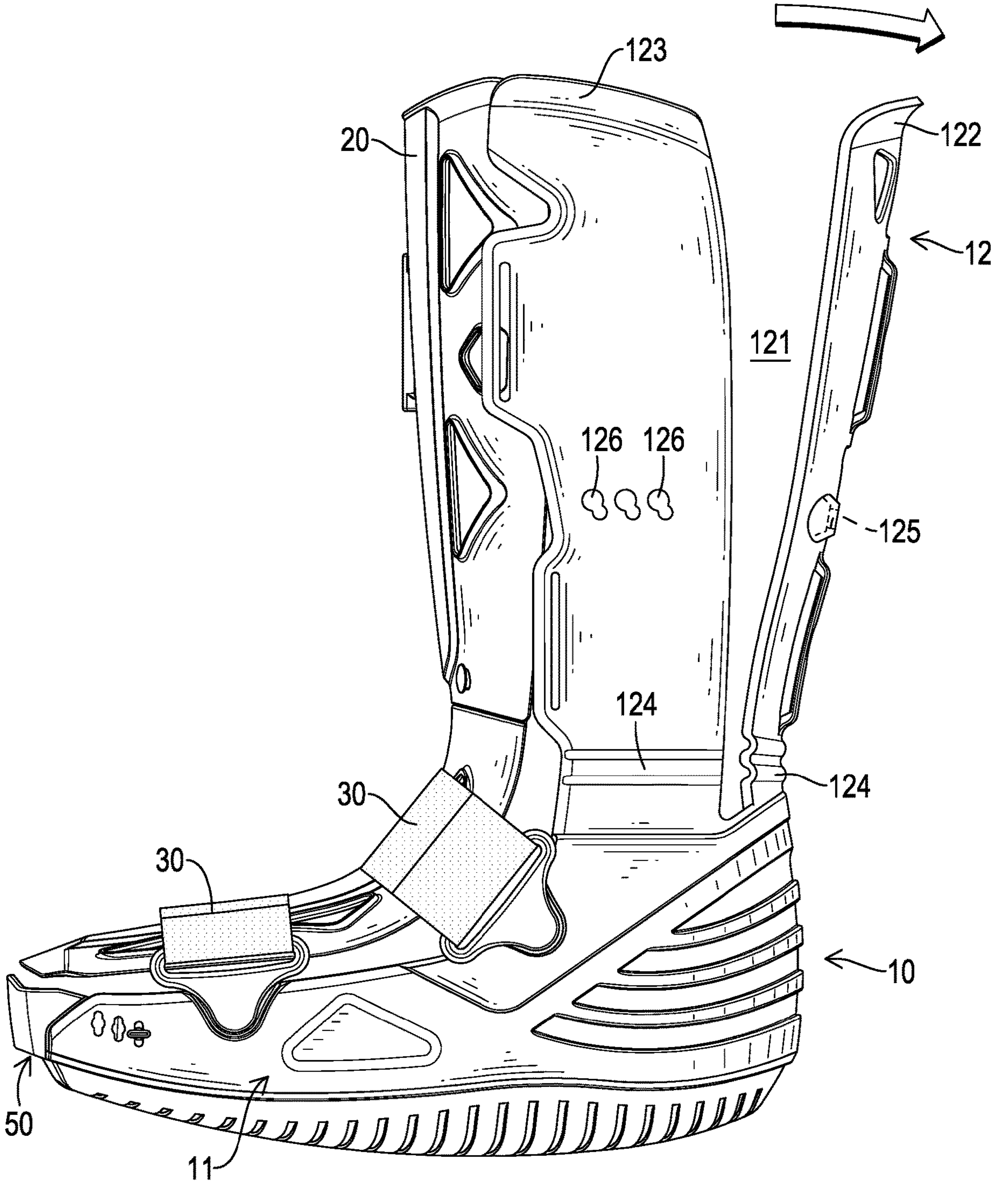
FIG. 4 is an operational lateral side view of the rehabilitation boot in FIG. 1.

With reference to FIGS. 1 to 4, a rehabilitation boot in accordance with the present invention has a main body 10, a front plate 20, multiple elastic bands 30, two restricting bands 40, and a toe cover 50.

With reference to FIGS. 1 to 4, the main body 10 has a base 11 and a tubular sleeve 12. The base 11 is configured to receive a foot of a patient and has a front end, a rear end, and two lateral walls 111. The front end and the rear end of the base 11 are opposite in position. The two lateral walls 111 are parallel to each other and extend to the front end of the base 11. Each one of the two lateral walls 111 has multiple engaging holes 112 arranged toward the front end of the base 11 at intervals.

With reference to FIGS. 1 to 4, the tubular sleeve 12 is integrally formed at the rear end of the base 11 and upward extends opposite to the base 11. The tubular sleeve 12 has an opening, two cuts 121, a rear plate 122, two lateral plates 123, and two fixing holes 124. The opening of the tubular sleeve 12 is disposed at a front side of the tubular sleeve 12. The two cuts 121 longitudinally extend from a top of the tubular sleeve 12 to the base 11. Each one of the two cuts 121 has a width gradually increasing toward the base 11. The tubular sleeve 12 is divided by the two cuts 121 to form the rear plate 122 opposite to the opening of the tubular sleeve 12 and the two lateral plates 123 respectively disposed at two opposite sides of the rear plate 122. Each one of the rear plate 122 and the two lateral plates 123 has multiple bendable portions 124 being corrugated and can be bent easily. The two fixing holes 125 are separately formed through the rear plate 122. Each one of the two lateral plates 123 has multiple adjusting holes 126 arranged at intervals.

With reference to FIGS. 1 to 4, the front plate 20 is bended, is connected to the main body 10 via the multiple elastic bands 30, and covers the opening of the tubular sleeve. The front plate 20 and the elastic bands 30 are common knowledge and are not further described herein.

Figure 5:
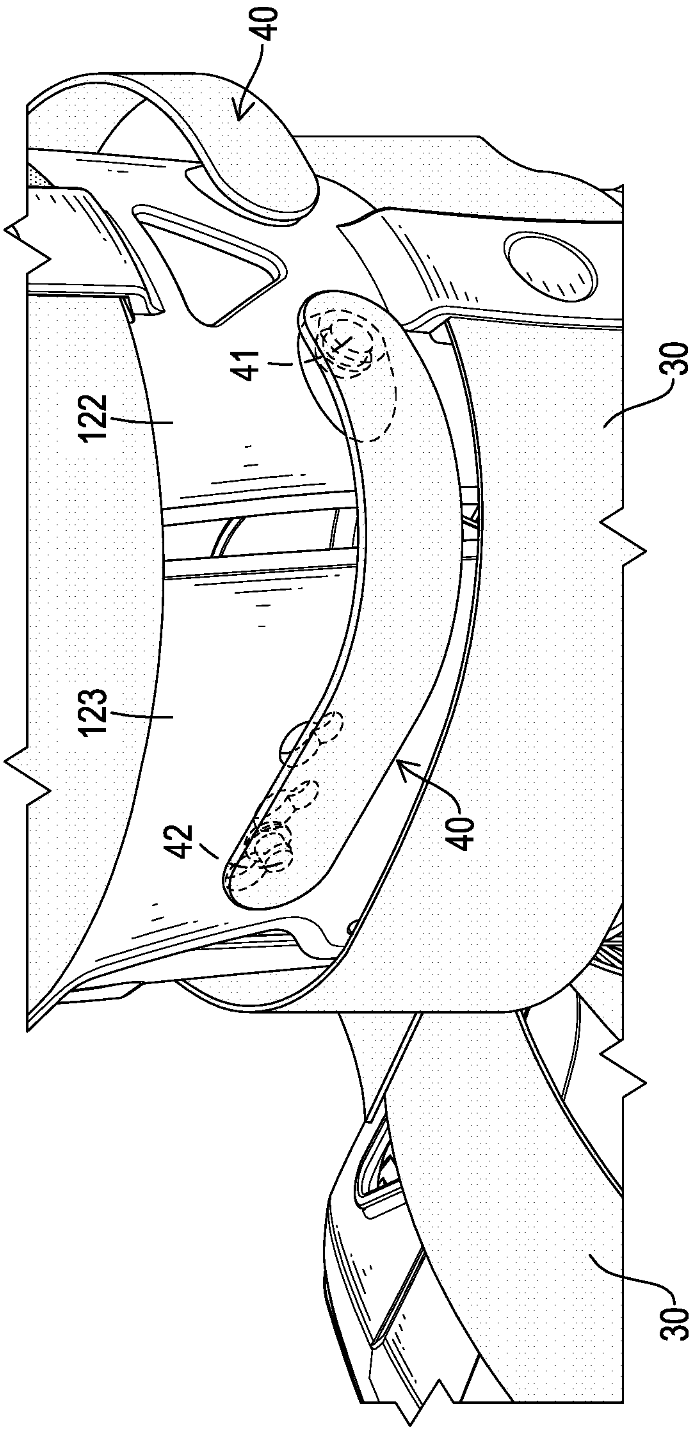
FIG. 5 is an enlarged perspective view of the rehabilitation boot in FIGS. 1.

With reference to FIGS. 1 to 5, each one of the two restricting bands 40 has two opposite ends, a fixing protrusion 41, and an adjusting protrusion 42. The fixing protrusion 41 and the adjusting protrusion 42 are respectively disposed at the two opposite ends of the restricting band 40. The two ends of one of the two restricting bands 40 are respectively connected to the rear plate 122 and one of the two lateral plates 123, and the two ends of the other restricting band 40 are respectively connected to the rear plate 122 and the other lateral plate 123. Please refer to FIGS. 4 and 5: one of the two restricting bands 40 is further described below: the fixing protrusion 41 engaging with the one of the two fixing holes 125 formed through the rear plate 122, the adjusting protrusion 42 engaging with one of the adjusting holes 126 of a corresponding one of the two lateral plates 123.

Figure 6:
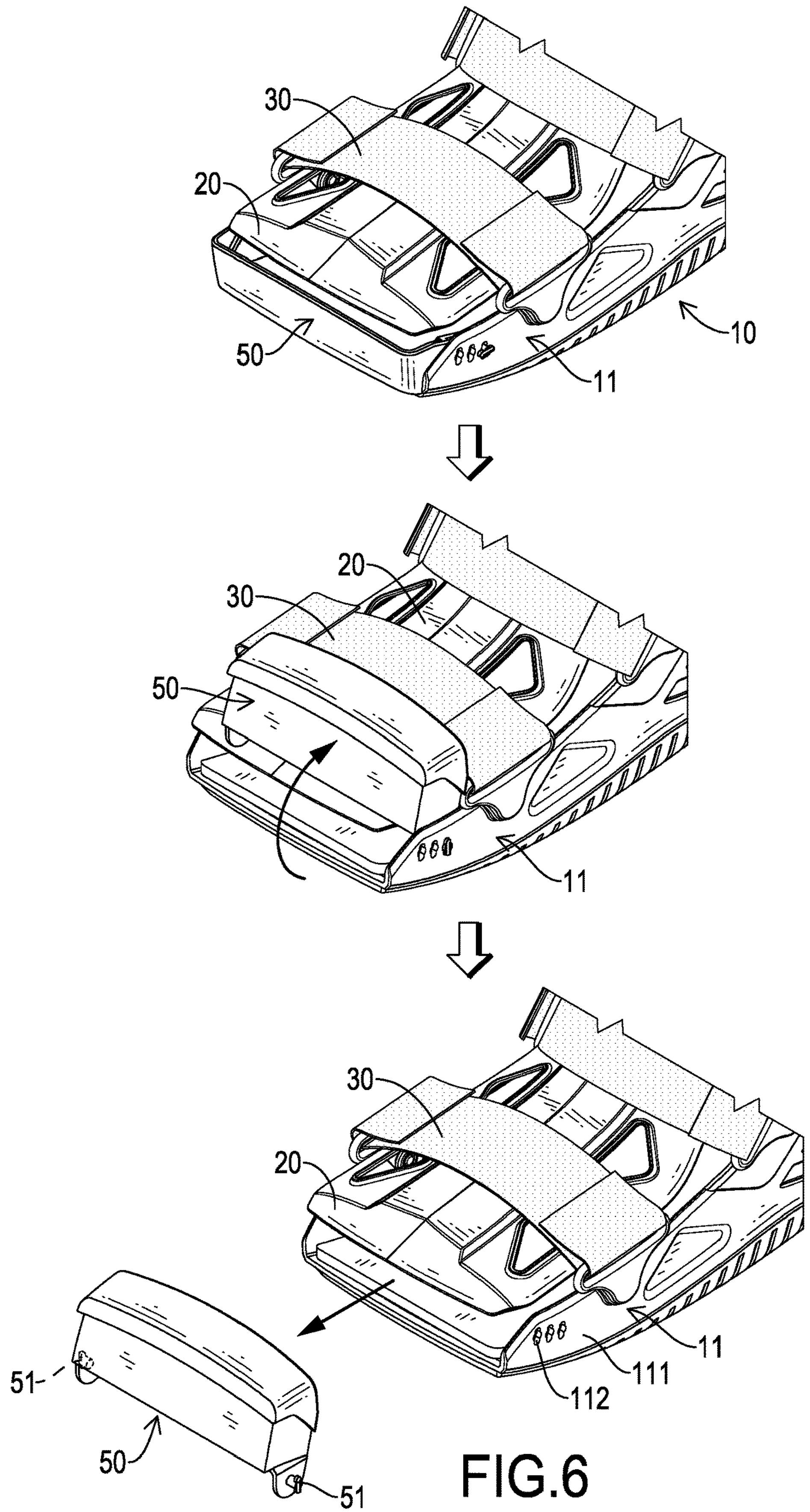
FIG. 6 is an operational perspective view of the rehabilitation boot in FIG. 1.

With reference to FIGS. 1 to 6: the toe cover 50 has two engaging elements 51 respectively disposed at two opposite sides of the toe cover 50. The two engaging elements 51 of the toe cover 50 respectively engage with the engaging holes

112 of the two lateral walls 111 of the base 11. The toe cover 50 can pivot relative to the base 11 and can be easily detached from the base 11.

With reference to FIGS. 1 to 6: the tubular sleeve 12 divided into the rear plate 122 and the two lateral plates 123 can be easily expanded by a swelling broken calf of a patient. Therefore, the swelling broken calf is free from pressing by the tubular sleeve 12. The wearing experience of the rehabilitation boot can be promoted accordingly.

In addition, the adjusting protrusion 42 of each restricting band 40 can selectively engage with one of the adjusting holes 126 of a corresponding one of the lateral plates 123. Therefore, the tubular sleeve 12 can be adjusted according to the recovery conditions of the broken calf.

Furthermore, the two engaging elements 51 of the toe cover 50 can selectively engage with the engaging holes 112 of the two lateral walls 111. Therefore, the toe cover 50 can be moved forward or backward to fit the size of the patient's feet.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A rehabilitation boot comprising:
- a main body having
  - a base having a front end and a rear end opposite to each other;
  - a tubular sleeve integrally formed at the base and having
    - an opening disposed at a front side of the tubular sleeve; and
    - two cuts longitudinally extending from a top of the tubular sleeve to the base to divide the tubular sleeve into a rear plate and two lateral plates respectively disposed at two opposite sides of the rear plate;
- a front plate connected to the main body via multiple elastic bands; and
- two restricting bands, each one of the two restricting bands has two opposite ends;
- wherein the two ends of one of the two restricting bands are respectively connected to the rear plate and one of the two lateral plates, the two ends of the other one of the two restricting bands are respectively connected to the rear plate and the other one of the two lateral plates wherein the tubular sleeve has two fixing holes separately formed through the rear plate; each one of the two lateral plates has multiple adjusting holes arranged at intervals; each one of the two restricting bands has a fixing protrusion and an adjusting protrusion respectively disposed at the two ends of the restricting band; and the fixing protrusion of each one of the two restricting bands engages with one of the two fixing holes formed through the rear plate, and the adjusting protrusion of the restricting band engages with one of the multiple adjusting holes of a corresponding one of the two lateral plates.

2. The rehabilitation boot as claimed in claim 1, wherein each one of the rear plate and the two lateral plates has a bendable portion being corrugated for ease of bending.

3. The rehabilitation boot as claimed in claim 2, wherein the bendable portion of each one of the rear plate and the two lateral plates is disposed adjacent to the base.

4. The rehabilitation boot as claimed in claim 3, wherein
- the base has two lateral walls parallel to each other and extending to the front end of the base, and each one of the two lateral walls has multiple engaging holes arranged toward the front end of the base at intervals;
- the rehabilitation boot has a toe cover having two engaging elements respectively disposed at two opposite sides of the toe cover; and
- the two engaging elements of the toe cover are respectively engaged with two engaging holes of the two lateral walls.

5. The rehabilitation boot as claimed in claim 3, wherein each one of the two cuts has a width gradually increasing toward the base.

6. The rehabilitation boot as claimed in claim 2, wherein
- the base has two lateral walls parallel to each other and extending to the front end of the base, and each one of the two lateral walls has multiple engaging holes arranged toward the front end of the base at intervals;
- the rehabilitation boot has a toe cover having two engaging elements respectively disposed at two opposite sides of the toe cover; and
- the two engaging elements of the toe cover are respectively engaged with two engaging holes of the two lateral walls.

7. The rehabilitation boot as claimed in claim 2, wherein each one of the two cuts has a width gradually increasing toward the base.

8. The rehabilitation boot as claimed in claim 1, wherein
- the base has two lateral walls parallel to each other and extending to the front end of the base, and each one of the two lateral walls has multiple engaging holes arranged toward the front end of the base at intervals;
- the rehabilitation boot has a toe cover having two engaging elements respectively disposed at two opposite sides of the toe cover; and
- the two engaging elements of the toe cover are respectively engaged with two engaging holes of the two lateral walls.

9. The rehabilitation boot as claimed in claim 8, wherein each one of the two cuts has a width gradually increasing toward the base.

10. The rehabilitation boot as claimed in claim 1, wherein
- the base has two lateral walls parallel to each other and extending to the front end of the base, and each one of the two lateral walls has multiple engaging holes arranged toward the front end of the base at intervals;
- the rehabilitation boot has a toe cover having two engaging elements respectively disposed at two opposite sides of the toe cover; and
- the two engaging elements of the toe cover are respectively engaged with two engaging holes of the two lateral walls.

11. The rehabilitation boot as claimed in claim 10, wherein each one of the two cuts has a width gradually increasing toward the base.

12. The rehabilitation boot as claimed in claim 1, wherein each one of the two cuts has a width gradually increasing toward the base.

13. The rehabilitation boot as claimed in claim 1, wherein each one of the two cuts has a width gradually increasing toward the base.

* * * * *